United States Patent [19]

Ulrich

[11] 4,135,506
[45] Jan. 23, 1979

[54] METHOD OF AND DEVICE FOR PINNING A FRACTURED VERTEBRA

[76] Inventor: Max B. Ulrich, Amselstr. 55, Ulm, Germany, 7900

[21] Appl. No.: 777,725

[22] Filed: Mar. 15, 1977

[30] Foreign Application Priority Data

Mar. 16, 1976 [DE] Fed. Rep. of Germany ....... 2610907

[51] Int. Cl.² .................. A61F 5/04; A61B 17/18; A61B 17/28
[52] U.S. Cl. ................ 128/92 B; 128/92 D; 128/92 E; 128/321
[58] Field of Search ............. 128/92 B, 92 D, 92 BA, 128/92 BC, 92 C, 92 E, 92 EA, 92 G, 92 R, 83, 69, 334 R, 321, 337; 3/1.9

[56] References Cited

U.S. PATENT DOCUMENTS

| 583,455 | 6/1897 | Bush | 128/92 D |
| 3,862,631 | 1/1975 | Austin | 128/92 B |
| 4,055,172 | 10/1977 | Ender et al. | 128/92 BC |

FOREIGN PATENT DOCUMENTS

227510 6/1969 U.S.S.R. ................. 128/92 R

OTHER PUBLICATIONS

"Forceps for Grasping and Holding Bone Plates" by Meyer M. Stone, Journal of Bones & Joint Surgery, vol. 31A, No. 3, Jul. 1949, p. 665.

*Primary Examiner*—Ronald L. Frinks
*Attorney, Agent, or Firm*—Karl F. Ross

[57] ABSTRACT

A bone pin for a fractured vertebra has a pair of ends, a bend between the ends, and at least one laterally extending lug at one of the ends. A nonstraight hole is drilled in a vertebra or between two vertebrae and the pin is inserted by means of a special forceps into this hole. Thereafter the lug or lugs of the pin is screwed to the vertebra. Such a pin can be applied transabdominably or transthoracically, and can even be used to pin the odontoid process of the second cervical vertebra.

12 Claims, 11 Drawing Figures

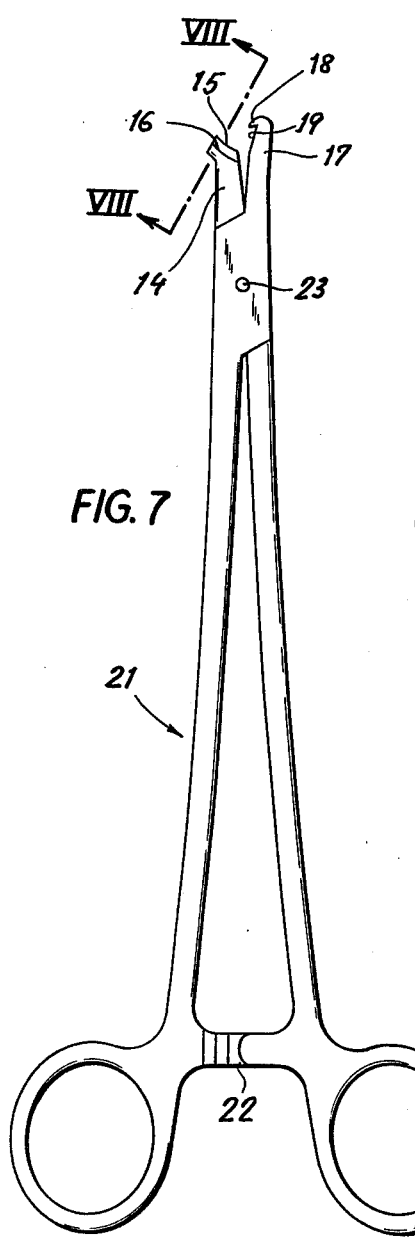
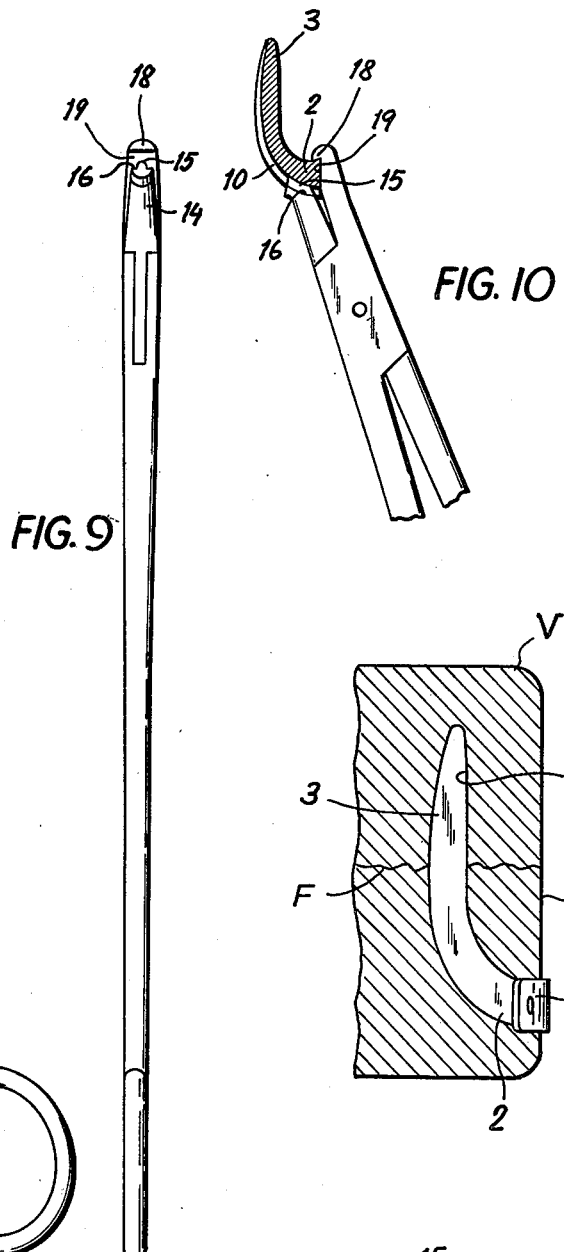
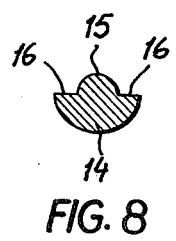

METHOD OF AND DEVICE FOR PINNING A FRACTURED VERTEBRA

CROSS-REFERENCE TO RELATED APPLICATION

This application is related to the commonly owned and concurrently filed patent application Ser. No. 777,691, the entire disclosure of which is herewith incorporated by reference.

FIELD OF THE INVENTION

The present invention relates to a pin, forceps, and method for bone surgery. More particularly, this invention concerns a pin and a tool for pinning a fractured vertebra.

BACKGROUND OF THE INVENTION

It is a well-known process to repair fractures of long or pipe bones by inserting so-called bone pins in the medullary cavities of these bones. In this manner, fractured hip joints, fingers, legs and the like can be pinned so that an extensive and often impossible-to-apply cast can be done away with.

When, however, a vertebra is fractured, it is necessary either to fit the patient with a cumbersome and often ineffective cast, or to apply an external bone splint to the fractured vertebra or vertebrae. In the most common splinting method, an orthoplastic splint is secured via ligatures to the posterior clinoid process of the fractured vertebra. It has also been suggested to screw a metal plate to the vertebra to either side of the fracture thereof.

These last-described methods have the considerable disadvantage that it is necessary to apply them to the back or dorsal side of the vertebra. This is the side along which the nerve column runs, so that a substantial risk of damaging this nerve column and severely injuring the patient is present. Furthermore the relatively weak vertebral arches do not provide a good fixation for the known splints.

OBJECTS OF THE INVENTION

It is therefore an object of the present invention to provide an improved method of treating a fractured vertebra.

Another object of the invention is to provide a bone pin usable in a fractured vertebra.

A further object is to provide an improved method of and tool for setting such a bone pin in a fractured vertebra.

Yet another object of this invention is to provide a surgical procedure and bone pin that allows the odontoid process of the second cervical vertebra to be pinned, a surgical procedure that has hitherto been considered impossible.

SUMMARY OF THE INVENTION

These objects are attained in accordance with the present invention in a bone pin having a pair of ends, a bend between these ends, and at least one laterally extending lug at one of the ends which is securable to a vertebra in which a nonstraight hole has been bored to receive the pin. This nonstraight bore is formed in accordance with the above-cited copending patent application.

According to further features of this invention, the pin has a pair of portions at either side of the bend. The one portion is substantially straight and pointed, whereas the other portion is largely bent and extends generally perpendicularly to the one portion and is provided at its end with a pair of laterally extending lugs. These lugs extend in opposite directions to a plane including both of the portions of the pin, and are curved inwardly and formed with throughgoing holes so that they can easily be screwed to the side or front of the vertebra.

Thus in accordance with the present invention it is possible to pin a fractured vertebra from the side or front, avoiding injury to the lumbal nerve column. Thus the application of the pin is transabdominal or transthoracical. First an arcuate hole is drilled in the vertebra with the drill described in the above-cited copending application, then the pin is inserted in this hole and finally the lugs are screwed to the side or front surface of the body of the vertebra.

According to yet another feature of this invention the two generally perpendicular portions of the pin therefore define a convex side and a concave side. A groove extends the full length of the convex side and opens at the ends of of the pin. In addition the convex side is formed adjacent the lugs with a recess. A forceps according to this invention has a pair of approachable jaws one of which is formed with a ridge which can fit snugly in the groove and the other of which is formed as a claw snugly engageable with the recess. This forceps therefore can tightly hold the pin and allow it to be carefully inserted in the arcuate bore through the fractured vertebra.

It is also possible in accordance with the present invention to use the pin to secure the odontoid process of the second cervical vertebra. To do this, access is had to the second cervical vertebra whose odontoid process is broken directly under and to the right of the chin of the patient. Such pinning eliminates the normally carried out fusion of the two cervical vertebrae with the inherent immobility of the head that results.

BRIEF DESCRIPTION OF THE DRAWING

The above and other objects, features and advantages of the present invention will become more readily apparent from the following description, reference being made to the accompanying drawing in which:

FIG. 7 is a side view of an insertion forceps usable with the bone pin according to this invention;

FIG. 8 is a section taken along line VIII — VIII of FIG. 7;

FIG. 9 is an edge view of the forceps according to this invention;

FIG. 10 is a side view of the end portion of the forceps of FIG. 7 shown holding a bone pin according to this invention; and FIG. 11 shows the bone pin according to this invention set in a fractured vertebra.

SPECIFIC DESCRIPTION

Figure 1:
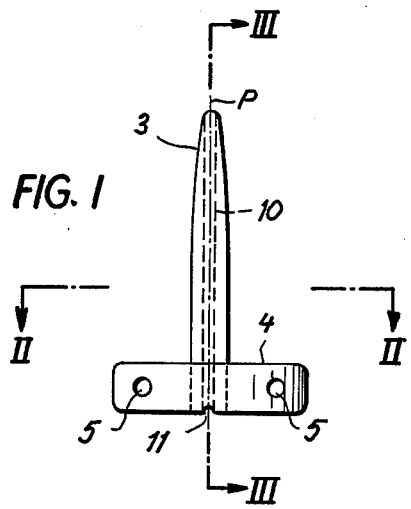
FIG. 1 is a part view of a bone pin according to this invention.
Figure 3:
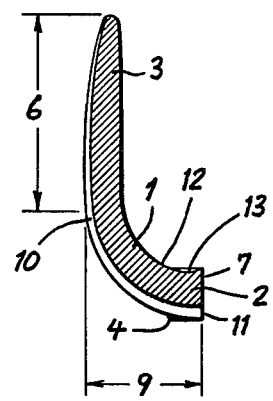
FIGS. 2 and 3 are sections taken along lines II — II and III — III, respectively, of FIG. 1.
Figure 2:
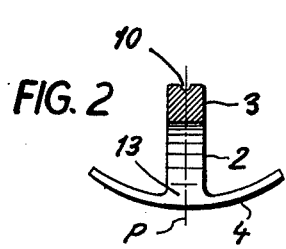

As shown in FIGS. 1–3 the bone pin according to this invention has a pair of legs 2 and 3 with respective dimensions 9 and 6 separated at a bend 1. These legs 2 and 3 lie in a common plane P and the dimension 6 is substantially greater than the dimension 9. The tip of the leg 3 is pointed and the leg 2 is provided with a pair of laterally extending lugs 4 each having a respective throughgoing hole 5. These lugs are curved toward the leg 3 and lie on an imaginary cylinder having an axis on the plane P.

A groove 10 in the plane P extends along the convex outer side of the two legs 2 and 3 and opens at the flat end face 7 of the leg 2 at 11. In addition the upper side 12 of the leg 2 is formed with a recess 13 directly across in the plane P from the groove 11.

The pin of FIGS. 1–3 is used to pin two parts of a vertebra. Thus this pin is relatively large and has a relatively long dimension 6.

Figure 4:
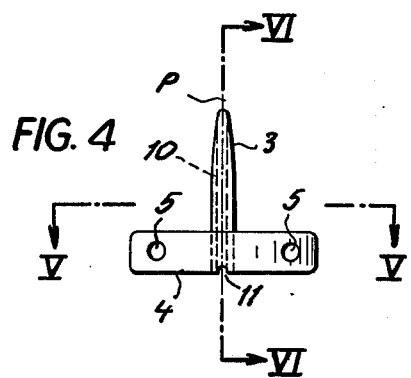
FIG. 4 is a view similar to FIG. 1 of another bone pin according to the present invention.
Figure 6:
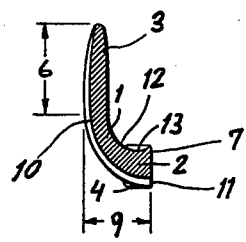
FIGS. 5 and 6 are sections taken along lines V — V and VI — VI, respectively, of FIG. 4.
Figure 5:
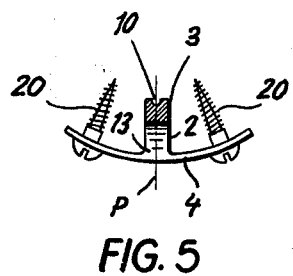

The pin of FIGS. 4–6 is identical to that of FIGS. 1–3 except that it is somewhat smaller, being intended to pin the odontoid process of the second cervical vertebra. Such pinning of an odontoid process has never before been considered possible.

FIGS. 8–10 show a forceps 21 provided adjacent the handles with a hemostat-type clamp 22 and having a pair of approachable jaws 14 and 17 secured together at a box pivot 23. The jaw 14 has a surface 16 upwardly from which extends an elongated ridge 15 dimensioned exactly to fit within the groove 10. The jaw 17 has a surface 19 dimensioned to fit snugly against the surface 7 and has a claw formation 18 adapted to engage in the recess 13 as shown in FIG. 10. Thus it is possible with this clamp or forceps 21 to tightly hold a pin such as shown in FIGS. 1–3 or in FIGS. 4–6.

In use an arcuate bore B is formed in a vertebra V extending across a fracture F therein and opening at a surface S of the vertebra V. After the bore B has been drilled using the tool described in the above-cited copending application, a pin is grasped as shown in FIG. 10 by the forceps 21 and is inserted into this bore B from the side or front surface of the vertebra V. Thereafter screws 20 as shown in FIG. 5 are inserted through the holes 5 and threaded into the vertebra V so as to secure the pin tightly in place.

The pin according to this invention is formed of a metal such as stainless steel that is capable of withstanding superheated steam 134° C. so that it can be autoclaved before insertion.

I claim:

1. A bone pin having a pair of coplanar ends substantially at right angles to one another, a bend between said ends said ends and said bend lying substantially in a common plane, and at least one laterally extending lug at one of said ends securable to a vertebra in which said pin is set, said lug lying generally perpendicular to said plane and the other of said ends being pointed for setting the pin in said vertebra.

2. A bone pin comprising:
an elongated member having a front end insertable in a vertebra, a rear end adapted to protrude therefrom and substantially perpendicular to said front end and coplanar therewith, and a bend connecting said ends; and
a pair of lugs extending laterally oppositely from said rear end and securabe to said vertebra.

3. The bone defined in claim 2 wherein said lugs are curved and shaped to fit around a vertebra.

4. The bone pin defined in claim 2 wherein said portion at said one end is curved and the other portion is generally straight.

5. The bone pin defined in claim 2 wherein the other of said ends is pointed.

6. The bone pin defined in claim 2 wherein said pin has a concave side and a convex side, said portions being formed with a groove extending the full length of said convex side and opening at said lugs.

7. The bone pin defined in claim 6 wherein said pin is formed on said concave side at said lugs with a recess.

8. In combination with the bone pin of claim 7, a forceps having a pair of approachable jaws one of which is formed with a ridge snugly fittable with said groove and the other of which is formed as a claw engageable in said recess.

9. The bone pin defined in claim 2 wherein said lugs are formed with throughgoing holes adapted to receive screws.

10. A method of pinning a fractured vertebra comprising the steps of:
boring in the fractured vertebra a nonstraight hole extending across the fracture therein and opening at a surface thereof;
inserting in said hole a nonstraight bone pin having a pair of lugs; and
screwing said lugs to said surface.

11. The method defined in claim 10 wherein said surface is the side surface of said vertebra.

12. The method defined in claim 10 wherein said surface is the front surface of said vertebra.

* * * * *